United States Patent
Ilan (10) Patent No.: US 7,287,983 B2
(45) Date of Patent: Oct. 30, 2007

(54) POLYMERIC DENTAL IMPLANT

(75) Inventor: Daniel Ilan, Nofit (IL)

(73) Assignee: Polydent Medical Devices Ltd., Ramat Gan (IL)

( * ) Notice: Subject to any disclaimer, the term of this patent is extended or adjusted under 35 U.S.C. 154(b) by 334 days.

(21) Appl. No.: 10/476,577

(22) PCT Filed: Apr. 21, 2002

(86) PCT No.: PCT/IL02/00316

§ 371 (c)(1),
(2), (4) Date: May 14, 2004

(87) PCT Pub. No.: WO02/089694

PCT Pub. Date: Nov. 14, 2002

(65) Prior Publication Data
US 2004/0209228 A1    Oct. 21, 2004

(30) Foreign Application Priority Data

May 3, 2001    (IL) .................................. 142933

(51) Int. Cl.
*A61C 8/00* (2006.01)
(52) U.S. Cl. .................. 433/175; 433/201.1; 433/172
(58) Field of Classification Search ........ 433/172–176, 433/201.1
See application file for complete search history.

(56) References Cited

U.S. PATENT DOCUMENTS

| | | | |
|---|---|---|---|
| 3,919,773 A * | 11/1975 | Freeman | 433/175 |
| 4,738,623 A | 4/1988 | Driskell | |
| 4,904,534 A * | 2/1990 | Nagai | 428/457 |
| 5,002,488 A * | 3/1991 | Homsy | 433/169 |
| 5,397,235 A * | 3/1995 | Elia | 433/173 |
| 5,558,517 A * | 9/1996 | Shalaby et al. | 433/201.1 |
| 6,042,380 A * | 3/2000 | De Rowe | 433/173 |
| 6,132,214 A * | 10/2000 | Suhonen et al. | 433/201.1 |
| 6,537,070 B1 * | 3/2003 | Stucki-McCormick | 433/174 |
| 6,840,770 B2 * | 1/2005 | McDevitt | 433/173 |

FOREIGN PATENT DOCUMENTS

| | | |
|---|---|---|
| EP | 0 901 773 A | 3/1999 |
| WO | 94 24956 A | 11/1994 |
| WO | 99 29254 A | 6/1999 |
| WO | 00 47127 A | 8/2000 |

* cited by examiner

Primary Examiner—Cary E. O'Connor
(74) Attorney, Agent, or Firm—Lowe Hauptman Ham & Berner LLP (57) ABSTRACT

The present invention relates to a polymeric implant, especially useful for dental medicine. More specifically, the present invention relates to a polymerizable device comprising an artificial tooth's root and an abutment anchored therein and to a kit comprising interalia the same. The present invention also relates to a method for implanting the implant in the alveolar bore of previously extracted tooth.

27 Claims, 4 Drawing Sheets

FIGURE 4

POLYMERIC DENTAL IMPLANT

FIELD OF THE INVENTION

The present invention relates to a polymeric implant, especially useful for dental medicine. More specifically, the present invention relates to a polymerizable device comprising an artificial tooth's root and an abutment anchored therein and to a kit comprising interalia the same. The present invention also relates to a method for implanting said implant in the alveolar bore of previously extracted tooth.

BACKGROUND OF THE INVENTION

As the lifespan of people has increased, so has the need for permanent dental replacements. Restorative dentistry encompasses efforts to conserve and restore decayed, defective, missing, and traumatically injured teeth, thereby promoting the dental health and achieving the aesthetic desires of the patient. An example of a prosthetic device is the dental implant, which is surgically positioned within the mandibular or maxillary alveolar bone. In the dental field, polymers are recognized as important components of composite restorative materials.

There are three main flaws with the traditional implants: the screws which hold the prosthetic tooth into the implant come loose; two separate surgeries are required (in most implant); and there is loss of bone material around the top of implants, resulting in as much as a 15% failure rate in some areas of the jaw.

Another problem with dental implants is that they are rather invasive and occasionally rejected by the body and expelled from the implantation site, such as the tooth socket (alveolus). Another concern is that current techniques employ repetitive surgery, implantation, healing and correction of the prosthesis. These procedures are typically repeated as many times as necessary to achieve the desired dental prosthesis implantation to the bone, as well as the appropriate stabilization. Consequently, these techniques are typically associated with a great deal of pain and inconvenience to the patient, as well as with the expenditure of excessive efforts and time by the oral surgeon, thereby resulting in higher treatment costs.

Therefore, there is a need for a device, such as a dental implant, and a method for the implantation of the device that not only enhances the opportunity for fixation of the device in the desired location, thereby increasing the functionality of the device, but also eases the pain, discomfort, inconvenience and cost realized by both the patient and the dental surgeon. The present invention is directed towards meeting these and other needs.

One type of dental implant has a first implant member for placement in an osteotomy site in the alveolar bone of a patient. Following healing, a head member, commonly called an abutment, is mounted in or on the first implant member and a tooth simulating prosthesis or crown is then mounted on the abutment. A successful system of this type is disclosed in U.S. Pat. No. 4,738,623. Although this procedure has been acceptable, the efficacy of the result is dependent upon the skill of the technician and is highly labor intensive and time consuming.

SUMMARY OF THE INVENTION

It is the primary object of the present invention to provide a useful polymeric dental implant, adapted to be implanted inside the bore of previously extracted tooth. Said implant is preferably comprising an artificial root, comprising a non shape-memory polymeric composition; adapted to be inserted in said bore, so said bore is substantially filled with said composition and an abutment comprising a proximal end, facing the oral cavity, having means to grip the structure of said implanted tooth; and distal end, efficiently anchored inside said polymeric composition.

It is in the scope of the present invention to provide an implant as defined above, comprising a multi-layer structure of more then one polymeric composition; wherein at least one external layer is located adjacent to the bone and is substantially composed of elastic polymer, suitable for either local or systemic delivery of compounds selected from drugs and other substances; and wherein at least one internal layer comprises of relatively non-elastic, non shape-memory and non biocompatible polymers, design to anchored effectively the abutment.

Thus, the said implant is preferably having at least one external polymeric layer, having a non-memory expandable tubular polymeric member, produced by either knitting, weaving, press-molding, inflating or foaming of said polymer composition. Said external layer is preferably biodegradable, and selected from poly l-lactic acid, poly d-lactic acid, poly d,l-lactic acid, polyglycolic acid, polyglactin, polydioxanone, polyglyconate, polyurethane, blends and copolymers thereof.

Similarly, the said implant is preferably having at least one external polymeric layer, comprises of acrylates, and more specifically, metaacrylate, at least partly crosslinked acrylates, polymethyl metaacrylates and derivatives thereof. In addition, said composition may comprises of polyacrylates additionally comprising additives, selected from hydroxyapatite, ceramics, fibrous materials, glass forming materials, phosphate salts, acrylates which were previously or partially polymerized, or phosphate salts or any other additive having means to increase the mechanical stability of the implant.

In the scope of the present invention is also the said implant defined above, having means to deliver drugs, such as biocides, steroidal anti-inflammatory agents, antiviral compound, analgesics, local anesthetics, anticoagulants, antihypertensive substances, vitamins and contrast media (borates and other salts).

It is well in the scope of the present invention, wherein the said implant comprising an abutment, which is efficiently anchored inside said polymeric composition by means1 selected from male or female threads, anchors and openings. Said anchors are preferably selected from tinted wing members, having means to protrude the external diameter of said abetment; sieve like members or gradually round construction in communication with said abutment. The abutment may comprises of main longitudinal axis, which is linear, kinked or concaved shape and is possibly and at least partially made of non-polymeric materials, selected from titanium alloys, Nitinol, iron ware, ceramic or any other composite materials.

It further acknowledged that the bore of previously extracted tooth is adapted, according to one particulate embodiment of the present invention, to accommodate the said polymeric implant by means selected from either increasing said bore's diameter so a wider substantially round cut is obtained or by shaping said cut to provide a non-round cut shape; or by increasing said bore depth. Hence, the said bore may have a non-even diameter along the longitudinal axis of said bore, so the diameter of the distal end of said bore is substantially wider then the diameter in its relatively proximal rim. Moreover, the bore may have either non-even or irregular shape.

It is another object of the present invention to present a novel kit of polymeric dental implant as defined above. The kit is comprises of the following parts: (a) a syringe having means to maintain and to inject the polymeric to the bore of previously extracted tooth; (b) an abutment, designed as an open-bore pipe, having communication with said serine and said bore, and (c) at least one polymeric composition to be injected inside the bore of previously extracted tooth.

Additionally or alternatively, the aforementioned kit comprising a polymeric sleeve, having one opening which is in communication with said abutment, adapted to be inflated in said bore and to accept the injected polymeric composition, so at the time to the injection, said sleeve is provided as a barrier between the bone and the polymerized composition. The sleeve may be selected from porous, woven, knitted, braided and non-woven material, and the kit may additionally comprise of a healing cup.

Yet another object of the present invention is to provide a useful method for implanting the polymeric implant as defined above. The method preferably comprises the step of injecting at least a portion of a polymeric composition so said composition is transferred from the syringe, via an abutment to a bore of previously extracted tooth, so said bore and said abutment are substantially filled with said polymeric composition. This method is preferably and additionally defined in the manner the abutment is effectively anchored in its distal end in the internal layer of said composition and further wherein the proximal end of said abutment is facing the oral cavity.

Most particularly, in the scope of the present invention is the method for implanting the polymeric implant as defined above, comprising the steps of (1) mounting a polymeric dental implant onto a balloon catheter; (2) introducing said balloon catheter into the bore of previously extracted tooth; (3) inflating said balloon so as to expand the polymeric dental implant; (4) removing the balloon catheter such that the polymeric dental implant remains in an expanded state inside said bore; so an external layer adjacent to the bone is provided; and lastly (5) injecting at least a portion of the polymeric composition so the polymeric composition is transferred from the syringe, via the abutment to said bore of providing thus the internal polymer layer. Said method is particularly preferred wherein said abutment is anchored in its distal end in the internal layer of said composition and further wherein the proximal end of said abutment is facing the oral cavity. Said method may additionally comprises of more then one step of injecting, so a multi-layer polymeric composition is provided, and may further comprises of a first step of accommodating either the shape or depth of the bore of previously extracted tooth. It is lastly acknowledged that the said accommodating step is preferably provided by means of drilling by said distal end of the bore to be of a wider diameter then the proximal rim of said bore.

BRIEF DESCRIPTION OF THE INVENTION

FIG. 1 also presents various abutments to be mounded in said polymeric compositions.

FIG. 2 thus presents a cross section of a bore of previously extracted tooth and a dental apparatus adapted to implant a polymeric sleeve, thus enabling the implantation of the outer polymeric composition according to the present invention.

DETAILED DESCRIPTION OF THE INVENTION

The current invention contemplates the usage of any prosthesis, which can be inserted into the bore of a tooth previously extracted, or alternatively, to such a bore which was additionally accommodated in either the maxilar or the mandibula bones in order to create a mechanically competent dental implant.

The following description is provided, along all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide for the deployment of said polymeric dental implant.

According one preferred embodiment of the present invention, a polymeric dental implant is provided. This novel implant adapted to be implanted inside the bore of previously extracted tooth and to provide an effective means to grip a structure of implanted tooth, comprising:
  (i) An artificial root, comprising a non shape-memory polymeric composition; adapted to be inserted in said bore, so said bore is substantially filled with said composition, and
  (ii) An abutment comprising a proximal end, facing the oral cavity, having means to grip the structure of said implanted tooth; and distal end, efficiently anchored inside said polymeric composition.

According to another preferred embodiment of the present invention, the aforementioned implant is provided, wherein it comprising a multi-layer structure of more then one polymeric compositions. Thus, said implant comprising at least one external layer that is located adjacent to the bone and is substantially composed of elastic polymer. This polymeric composition is suitable for either local or systemic delivery of compounds selected from drugs and other substances.

Moreover, the above-described implant comprises of at least one internal layer, which made of relatively non-elastic, non shape-memory and non-biocompatible polymers that design to anchored the abutment effectively.

Thus, polymeric compounds adapted to be implanted at the respectively external layer are those that known to be biocompatible and to have the ability to be drug impregnated. These compounds include, yet not limited to poly-l-lactic, poly-d-lactic and/or poly-d,l-lactic acids and the like, polyglycolic acid and the like, polyanhydrides and the like, polyphosphate ester and the like, polyurethanes of many compositions, or polyethylene. Some of those compounds are precursors for elastic matrices and some are non-elastic matrices.

For the internal layers, there are several polymeric compounds that are known to be with considerable strength such as polyacrylates and the like, and particularly polymethyl metaacrylate (PMMA). It is acknowledged that at least portion of said PMMA compositions comprises of monomers and oligomers at least partly polymerized, or alternatively not fully polymerized. It further acknowledged that polymerization of a mixture of heterogeneous composition comprising both fully polymerized and not fully polymerized monomers and/or oligimers yields with respectively low polymerization temperature, thus most suitable of medical utilizations.

Those raw materials may be used in their many forms, i.e., crystals, fibers, blocks, plates, etc. and in a wide range of molecular weights. Co-polymers and blends are applicable according to the present invention to form either porous or non-porous polymeric matrices.

Additionally, according to a preferred embodiment of the present invention, at least part of the hereto defined external layers comprising polymeric compositions that may be at least partially bio-stable or bio-absorbable. If bio-stable, a drug, as wildly defined in the present invention, may diffuse out of the polymer, such to the bone tissue.

Various compositions are suitable to be delivered either locally or systematically by the aforementioned polymeric implant. These release compositions are selected for drugs, and any other desired materials, including, yet not limited to one or more biocides, steroidal anti-inflammatory agents, antiviral compound, analgesics, local anesthetics, anticoagulants, antihypertensive substances, vitamins and contrast media.

According to another preferred embodiment of the present invention, steroidal anti-inflammatory agents may be used, comprising, but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

According to another preferred embodiment of the present invention, at least two antiviral compounds may be used, comprising, but not limited to acyclovir and interferon.

According to another preferred embodiment of the present invention, steroidal analgesics may be used, comprising, but not limited to aspirin, salicylic acid, diflunisal, morphine and its salts and the like.

According to another preferred embodiment of the present invention, antiseptic substances may be used comprising, but not limited to, cetylpyridinium chloride, benzalkonium chloride, chlorhexidine and the like.

According to another preferred embodiment of the present invention, antimycotic substances may be used comprising, but not limited to, cetyltrimethylammonium bromide and the like.

According to another preferred embodiment of the present invention, antifungals may be used comprising, but not limited to, polyoxyethylene nonylphenols, alkylaryl sulfonates, miconazole nitrate, metronidazole, trimethoprim and the like.

According to another preferred embodiment of the present invention, antiprotozoals may be used comprising, but not limited to, chloramphenicol, sulfamethoxazole and the like.

According to another preferred embodiment of the present invention, local anesthetics may be used comprising, but not limited to, salts of procaine, benzocaine, lidocain, procain, bupivacaine, tetracain, xylocaine, mepivacaine and their salts and the like; antiasthma drugs such as adrenaline, ephedrine, epinephrine, aminophylline, theophylline and the like.

According to another preferred embodiment of the present invention anticoagulants, may be used comprising, but not limited to, heparin and its salts, such as calcium and sodium heparin; bishydroxycoumarin and the like.

According to another preferred embodiment of the present invention antihypertensive, may be used comprising, but not limited to, methyldopa, hydralazine, clonidine, chiorothiazide, timolol, propanolol, metroprolol, prazosin hydrochloride, furosemide and the like.

According to another preferred embodiment of the present invention, vitamins may be used comprising, but not limited to, such as $B_6$, $B_{12}$ and C and the like.

According to another preferred embodiment of the present invention contrast media, may be used comprising, but not limited to, $BaSO_4$, iohexol and other iodine-containing substances and the like (x-ray), iron$^{(II,III)}$ oxide particles and other ferromagnetic materials (magnetic resonance imaging).

According to one particulate embodiment of the present invention, a part of the polymerization is taking place within a syringe. Said syringe is preferably designed as a delivery cannula having a two-barrel orifice, or multiple-barrel orifice, so that the material being injected into the bore of the previously extracted tooth is characterized with the following advantageous features:

(a) Part of the polymerization exotherm is already dissipated within the deployment syringe, reducing the heat developed in situ.

(b) Part of the shrinkage of the polymeric mass, a consequence of many polymerization processes, is hence already taken place, so the material will shrink minimally in situ.

(c) The presence of the inorganic non-polymerizing constituent, such as hydroxyapatite, calcium phosphate, is also contribute to minimize both the heat evolved as well as the extent of shrinkage attained by the material.

(d) The fact that part of the polymerization is thus taken place ex vivo is reducing significantly the presence of monomeric molecules in the material at implantation time, lowering, therefore, the vapor pressure of the material and diminishing substantially odor and other monomer-related problems.

(e) The fact that part of the polymerization was taken place ex vivo, is also simplifying the system, by making the use of a rapidly biodegradable external layer, performing as a barrier between the polymerizing material and the bone, unnecessary. Furthermore, it avoids creating a gap between the bone cement and the tissue, once this layer degraded. In addition, it makes easier the penetration of the polymerizing mass into the pores of the surface of the osseous tissue.

(f) The ceramic materials are chosen so it renders the device with enhanced osteoinductivity and contribute to the healing and regeneration of osseous tissue.

In another preferred embodiment of the present invention, the term abutment is referring to any stem, especially open-bored stem, having means to be in communication with the syringe and the bore to be reinforced with the aforementioned polymeric composition. Most particularly said term is referring to a polymeric made stem, or alternatively a stem partly made of titanium, Nitinol, steel or any other material mechanically adapted to be stable in dental system.

According to one preferred embodiment of the present invention, the polymeric dental implant and the method for its utilization is gathering the at least two additional characteristics: (a) The gap between the polymer and the bone, caused by the shrinking of the polymer, albeit partial, is significantly reduced by the pressure applied by the stem; and (b) the aforementioned method of implanting said implant and the forces applied on the polymerizing component allows to improve its physical interlocking within the pores and crevices of the osseous tissue as well as enhance its own mechanical properties by producing a denser and compact material.

It is further acknowledged that according one particular preferred embodiment of the present invention, the said abutment is gradually characterized by an external configuration of a screw and a central hollow cavity. Said screw form not only contributes to the fixation of the said abutment within the mass of the bone cement, but it is also making somewhat easier the retrieval of the implant, should it be required.

It is in the scope of the present invention wherein the central cavity is prepared previously to the implantation steps, preferably by either the factory or the clinic personal, with an internal component whose main tasks is to render the system with its ability to adjust to the spatial orientation requirements dictated by the position of the crown or any other alveolar structure to be attached to the implant. Thus, the abutment comprises in its inner bore a polymeric matrix and a reinforcing component. The former is preferable a polymer, having means to complying with directionality demands, by heating locally the inner abutment and bending it as required. The latter, on the other hand, is preferably made of diverse materials, such as ceramics, metals, carbons and polymers, and in various configurations, such as fibrous and particulate materials. A titanium sheath or any other effective material and the inner abutment are thus tightly and strongly attached, by chemical and/or by physical means.

It is further in the scope of the present invention wherein the abutment is prepared in the factory so it comprising the precursors of the polymeric composition, and when the abutment is mounted inside said bore of previously extracted tooth, said composition is exit the abutment and entering said bore. Thus, no syringe, comprising the polymeric composition is required. In this embodiment, the term syringe is referring only or partly to means to provide enough pressure to deliver said polymeric composition from the sealed abutment to said bore.

The term 'a bore of previously extracted tooth' is referring in the present invention to the root channels of the extracted tooth. Nevertheless, it is in the scope of the present inventions wherein said bore is pretreated by the dental surgeon so said bore is reshaped by means of drilling it along its longitudinal axis and additionally or alternatively, along to any dimension of said bore. One preferred embodiment is thus, a method for drilling the bone and thus reshaping it so the desired bore is obtained.

An alternative strategy to the inner rod worth exploring is the use of Nitinol-based structures, capitalizing on the well-known temperature-dependent dimensional response of this alloy.

Figure 1:
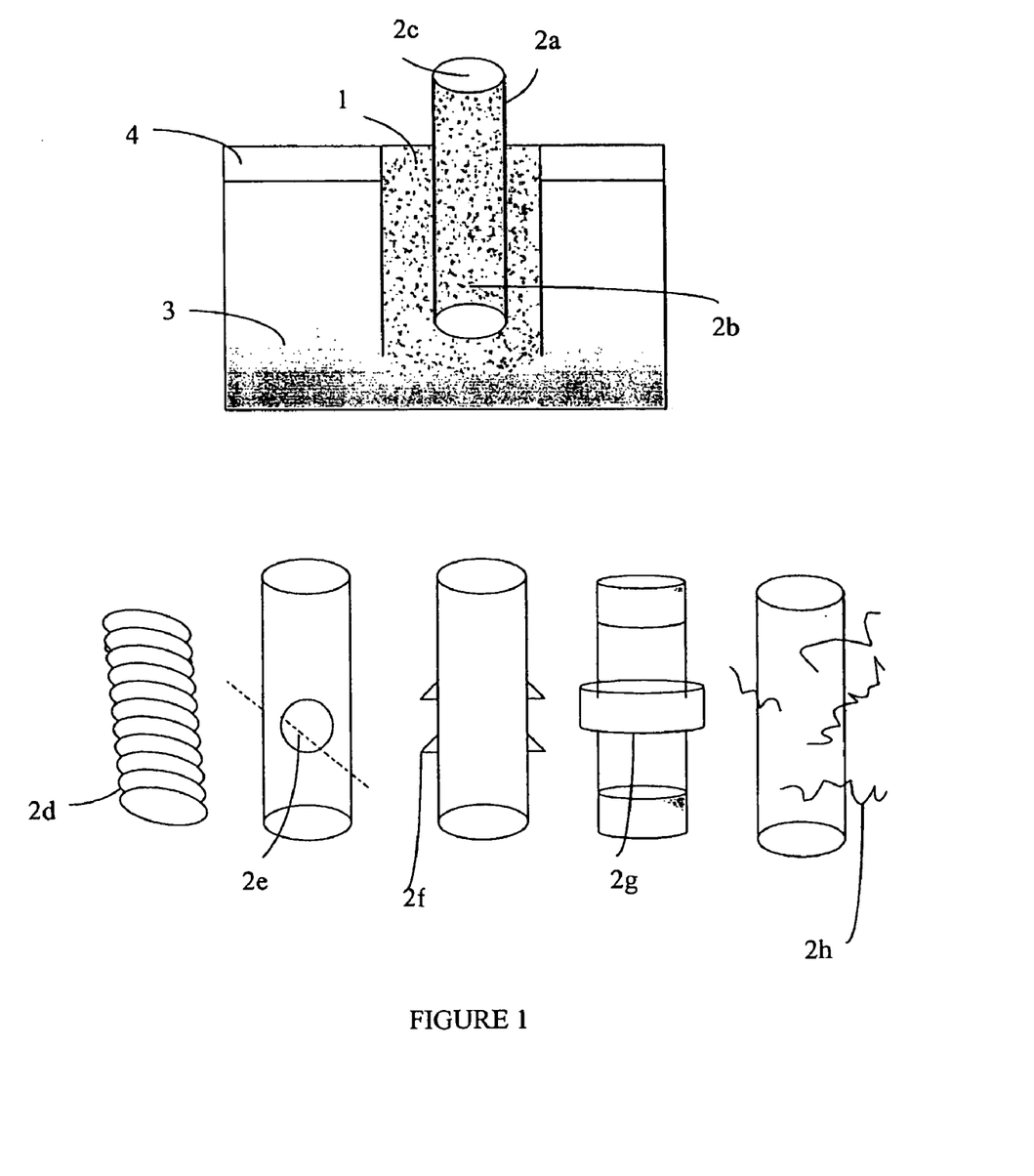
FIG. 1 presents a cross-section of a polymeric dental implant as defined in the present invention, comprising gradually homogenous polymeric composition and an abutment.

Reference is made now to FIG. 1, schematically presenting a side view of an alveolar bone (3) and gums above (4). In said bone, implanted the polymer implanted according to the present invention, comprising a polymeric composition (1) filing the bore of previously extracted tooth. An abutment is effectively anchored inside said polymeric composition, having a proximal rim (2a) facing the oral cavity, and distal rim (2b) inside said polymer. Said abutment preferably comprises an open bore (2c), having a polymeric composition. According to another preferred embodiment of the present invention, said abutment may additionally comprise means to be anchored inside the polymeric composition. Those means are selected, yet not limited to male or female threads (2d), opening (2e), wings (2f), construction (2g) or sieves (2h).

Figure 2:
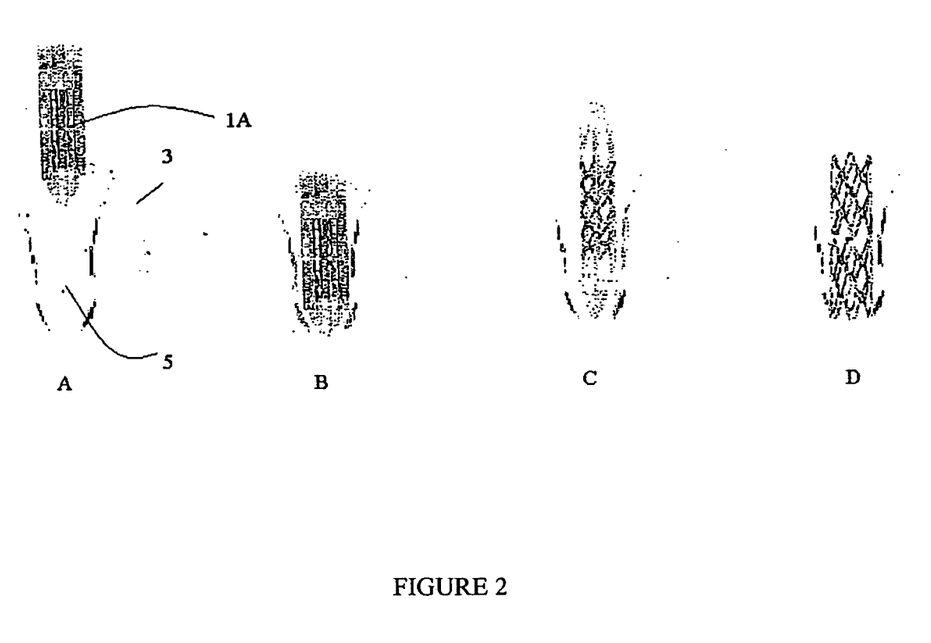
FIG. 2 presents the method for implanting the polymeric dental implant according to one preferred embodiment of the present invention.

Reference is made to FIG. 2, schematically presenting a side view of a polymeric sleeve (1a), grasped onto a chirurgical balloon, designed to be inserted in a bore of previously extracted tooth (5) (A). After the balloon is inserted into said bore (B), the chirurgical balloon is inflated, so the diameter of the polymeric sleeve is increasing to the desired diameter (C). Than the balloon is decreasing its diameter so its injection is provided (D) and wherein the polymeric sleeve is well anchored inside the alveolar bore.

It is well in the core of the present invention wherein said polymeric sleeve is mounted in said bore of previously extracted tooth by alternative means else then by inflating a balloon. Said alternative means are comprises of, yet not limited to injecting said polymeric composition, delivering it cement wise, or foam it into the said bore.

Figure 3:
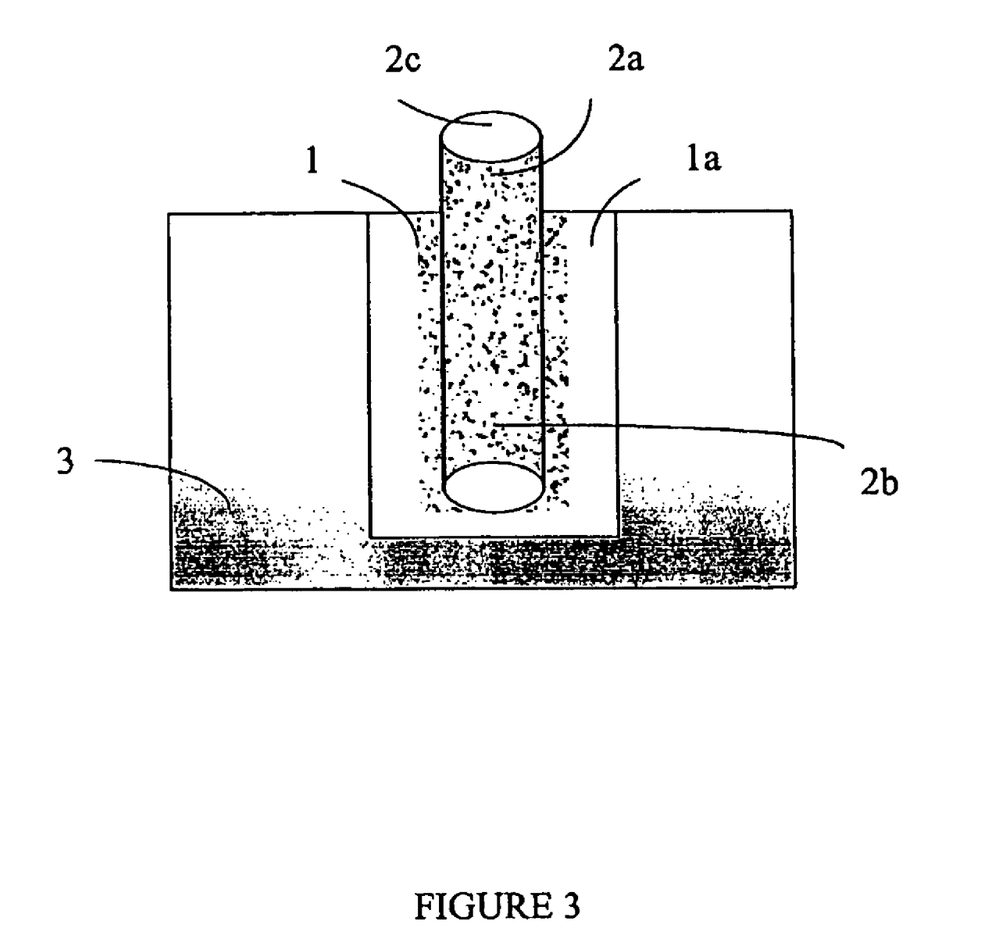
FIG. 3 presents a cross-section of a bore of previously extracted tooth comprising an outer layer (the polymeric sheet of FIG. 2), polymeric composition an abutment mounted thereof.

Similarly, a side view of a dental implant comprising more then one polymeric layer is presented in FIG. 3. The external polymeric layer (1a) is the said polymeric sleeve defines in FIG. 2, and the inner polymeric layer (1) is the polymeric composition, inserted via the bore of the said abutment.

Figure 4:
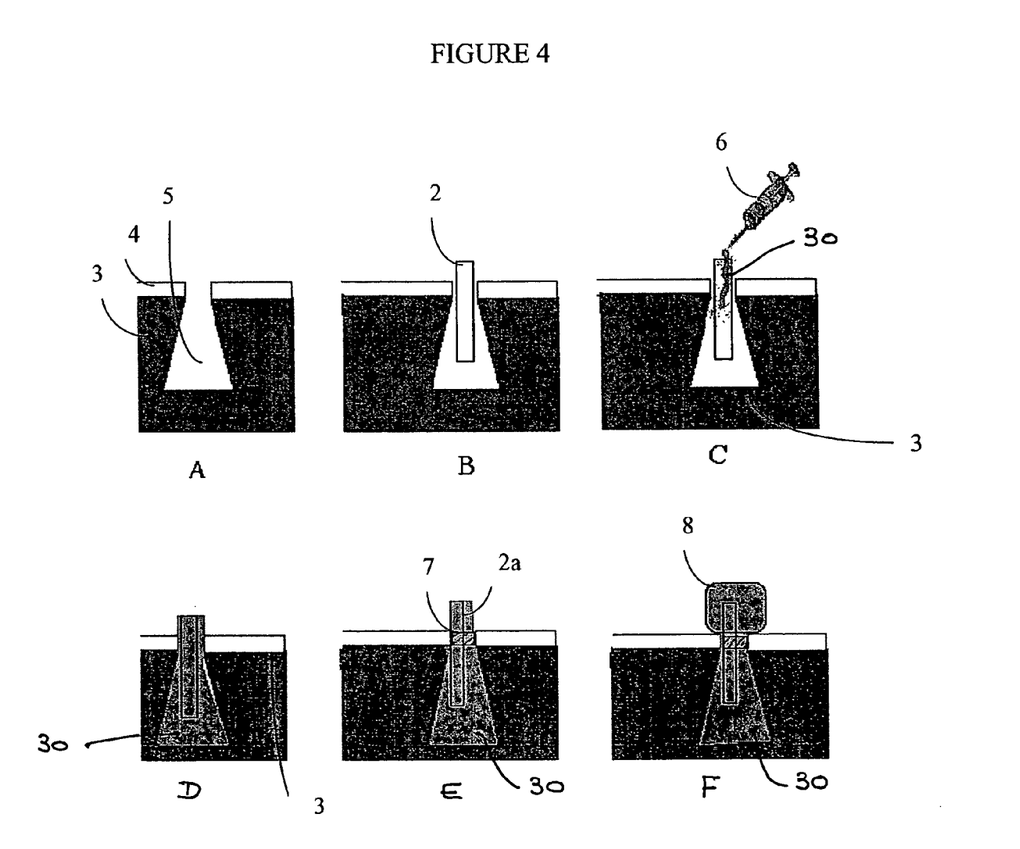
FIG. 4 presents the method for implanting the polymeric dental implant according to another preferred embodiment of the present invention.

Reference 4 is referring the implant according to the present invention, implant in an open bore of a root of a tooth previously extracted (5), preferably with non-even diameter along the longitudinal axis of said bore (A). An abutment (2) is at least partly inserted into said bore (B) and the polymeric composition (30) is injected from a syringe (6) into the bore of the abutment (2c). The bore of the bone is substantially filled (D) with at least one polymeric layer (30). The gums are sutured (E) with or without a healing cup so the abutment (2) is grasped by the gum (7). Lastly, a structure or a dental crown (8) is immobilized on the proximal rim of said abutment (2a) and the dental implant according to the present invention is obtained (F).

It is still in the scope of the present invention, wherein the sequence of the aforementioned procedure is so that the polymeric composition is inserted into the bore of previously extracted tooth, and only then the said abutment is mounted into said bore filled with said polymeric composition.

The invention claimed is:

1. A polymeric dental implant, configured to be implanted inside a bore created by a previous extraction of a tooth, said implant comprising:

a. an artificial root, comprising a non-shape-memory polymeric composition configured to be inserted in said bore, so said bore is substantially filled with said composition; and b. an abutment comprising a proximal end, facing the oral cavity, having means to grip the structure of an implanted tooth; and a distal end, efficiently anchored inside said polymeric composition; and c. a multi-layer structure of more than one polymeric composition; wherein at least one external layer is located adjacent to the bone and is substantially composed of elastic polymer, suitable for either local or systemic delivery of compounds selected from drugs and other substances; and wherein at least one internal layer comprises relatively non-elastic, non-shape-memory and non biocompatible polymers, designed to effectively anchor the abutment.

2. The implant according to claim 1, wherein the at least one external layer comprises a non-memory expandable tubular polymeric member, produced by either knitting, weaving, press-molding, inflating or foaming of said polymeric composition.

3. The implant according to claim 1, wherein the at least one external layer is at least in part biodegradable, and is selected from poly-l-lactic acid, poly-d,l-lactic acid, poly-d,l-lactic acid, polyglycolic acid, polyglactin, polydioxanone, polyglyconate, polyurethane, blends and copolymers of any of the above.

4. The implant according to claim 1, wherein the at least one internal layer comprises acrylates.

5. The implant according to claim 4, wherein said acrylates are selected from metaacrylate, at least partly crosslinked acrylates, polymethyl metaacrylates and derivatives of any of the above.

6. The implant according to claim 4, wherein said acrylates additionally comprise additives, selected from hydroxyapatite, ceramics, fibrous materials, glass forming materials, phosphate salts, acrylates which were previously or partially polymerized, phosphate salts, and any other additive which may increase the mechanical stability of the implant, and combinations of any of the above.

7. The implant according to claim 1, wherein the compound or drug to be delivered is selected from one or more of biocides, steroidal anti-inflammatory agents, antiviral compounds, analgesics, local anesthetics, anticoagulants, antihypertensive substances, vitamins and contrast media.

8. The implant according to claim 7, wherein the biocide to be delivered is selected from cetylpyridinium chloride, benzalkonium chloride, chlorhexidine, cetyltrimethylammonium bromide, polyoxyethylene, nonylphenols, alkylaryl sulfonates, miconazole nitrate, metronidazole, trimethoprim, chloramphenicol, sulfamethoxazole, cetramide, and any effective antibiotic.

9. The implant according to claim 7, wherein the steroidal anti-inflammatory agents to be delivered are selected from corticosteroids and any hydrocortisone-containing compositions.

10. The implant according to claim 7, wherein the local anesthetics or steroidal anti-inflammatory agents are selected from lidocaine, adrenaline, ephedrine, epinephrine, aminophylline, and theophylline.

11. The implant according to claim 1, wherein the abutment is efficiently anchored inside said polymeric composition by a mechanism selected from male or female threads, anchors and openings.

12. The implant according to claim 1, wherein the abutment comprises anchors selected from: tilted wing members extending past an external diameter of said abutment; sieve-like members; and a gradually round construction in communication with said abutment.

13. The implant according to claim 1, wherein the abutment comprises a longitudinal axis, which is linear, kinked or concaved shape.

14. The implant according to claim 1, wherein said abutment is at least partially made of non-polymeric materials, selected from titanium alloys, Nitinol, iron ware, ceramic or any other composite materials.

15. The implant according to claim 1, wherein said abutment is at least partially filled with polymeric precursors, to be inserted into said bore.

16. The implant according to claim 1, wherein said bore is further configured to accommodate said polymeric implant by one or more of: increasing said bore's diameter for a wider, substantially round cut to be obtained; shaping said cut for a non-round cut shape to be obtained; and increasing said bore depth.

17. The implant according to claim 1, wherein the bore accommodating the implant has a non-even diameter along a longitudinal axis of said bore, such that a diameter of a distal end of said bore is substantially wider than a diameter of a proximal end of said bore.

18. The implant according to claim 1, wherein the bore accommodating the implant has either a non-even or irregular shape.

19. A kit for a polymeric dental implant comprising an artificial root, the kit comprising:

(i) a syringe capable of maintaining a non-shape-memory polymeric composition and injecting said polymeric composition into a bore created by a previous extraction of a tooth;

(ii) at least one polymeric composition to be injected into said bore; and (iii) an abutment, designed as an open-bore pipe, in communication with said syringe and with said bore, wherein said abutment comprises a proximal end facing said bore, and comprises means to grip an implanted tooth, and a distal end, efficiently anchored inside said polymeric composition;

wherein said implant is configured to be implanted inside said bore; and wherein the artificial root comprises said at least one polymeric composition, configured to be inserted in said bore, such that said bore is substantially filled with said at least one polymeric composition.

20. The kit according to claim 19, additionally comprising a polymeric sleeve, having one opening which is in communication with said abutment, configured to be inflated in said bore and to accept the injected polymeric composition, such that upon said injection, said sleeve is a barrier between said implanted tooth and the polymeric composition.

21. The kit according to claim 20, wherein said sleeve is selected from porous materials, woven materials, knitted materials, braided materials, and non-woven materials.

22. The kit according to claim 19, additionally comprising a healing cup.

23. A method for implanting a polymeric dental implant configured to be implanted inside a bore created by a previous extraction of a tooth, wherein the implant comprises:

a. an artificial root, comprising a non-shape-memory polymeric composition configured to be inserted in said bore, such that said bore is substantially filled with said composition; and b. an abutment comprising a proximal end facing said bore and having means to grip the structure of an implanted tooth, and a distal end, efficiently anchored inside said polymeric composition;

the method comprising: injecting at least a portion of a polymeric composition such that said composition is transferred from the syringe, via an abutment to said bore such that said bore and said abutment are substantially filled with said polymeric composition;

wherein said abutment is effectively anchored by its distal end in an internal layer of said polymeric composition; and wherein the proximal end of said abutment is facing said bore.

24. The method for implanting a polymeric dental implant according to claim 23, the method comprising:
   a. mounting said polymeric dental implant onto a balloon catheter;
   b. introducing said balloon catheter into said bore;
   c. inflating said balloon so as to expand the polymeric dental implant;
   d. removing the balloon catheter such that the polymeric dental implant remains in an expanded state inside said bore, such that an external layer of the polymeric dental implant adjacent to said implanted tooth is provided; and
   e. injecting at least a portion of the polymeric composition so the polymeric composition is transferred from the syringe, via the abutment to said bore, thus providing an internal polymeric layer;

wherein said abutment is anchored in its distal end in the internal polymeric layer of said composition; and wherein the proximal end of said abutment is facing said bore.

25. The method for implanting the polymeric implant according to claim 23, additionally comprising more than one step of injecting, such that a multi-layer polymeric composition is provided.

26. The method according to claim 23, further comprising a first step of accommodating either a shape or a depth of said bore.

27. The method according to claim 23, wherein said accommodating is performed by drilling said bore such that a diameter of said bore adjacent to the distal end of the abutment is wider than a diameter of said bore adjacent to the proximal end of the abutment.

* * * * *